United States Patent [19]

Cahn

[11] Patent Number: 5,629,191
[45] Date of Patent: May 13, 1997

[54] METHOD OF MAKING A POROUS MATRIX PARTICLE

[75] Inventor: Frederick Cahn, Belmont, Mass.

[73] Assignee: Integra LifeSciences Corporation, Plainsboro, N.J.

[21] Appl. No.: 74,922

[22] Filed: Jun. 10, 1993

Related U.S. Application Data

[63] Continuation-in-part of Ser. No. 682,645, Apr. 9, 1991, abandoned, which is a continuation-in-part of Ser. No. 203,580, May 27, 1988, abandoned, which is a continuation of Ser. No. 688,630, Jan. 3, 1985, abandoned.

[51] Int. Cl.$^6$ ............................... C12N 5/06; C12P 21/02
[52] U.S. Cl. ..................... 435/395; 435/70.3; 435/174; 424/488; 424/484
[58] Field of Search ............................... 435/240.2, 70.3, 435/174; 424/488, 484

[56] References Cited

U.S. PATENT DOCUMENTS

| | | | |
|---|---|---|---|
| 4,252,759 | 2/1981 | Yannas et al. | 264/86 |
| 4,280,954 | 7/1981 | Yannas et al. | 260/123.7 |
| 4,350,629 | 9/1982 | Yannas et al. | 260/123.7 |
| 4,409,331 | 10/1983 | Lim | 435/178 |
| 4,448,718 | 5/1984 | Yannas et al. | 260/123.7 |
| 4,488,911 | 12/1984 | Luck et al. | 106/161 |
| 4,503,150 | 3/1985 | Triolo | 435/41 |
| 4,522,753 | 6/1985 | Yannas et al. | 260/123.7 |
| 4,537,860 | 8/1985 | Tolbert et al. | 435/240 |
| 4,546,083 | 10/1985 | Meyers et al. | 435/235 |
| 4,647,536 | 3/1987 | Mosbach et al. | 435/177 |
| 4,743,545 | 5/1988 | Torobin | 435/41 |
| 4,837,285 | 6/1989 | Berg et al. | 530/35.6 |
| 4,861,714 | 8/1989 | Dean et al. | 435/68 |
| 4,863,856 | 9/1989 | Dean et al. | 435/68 |
| 4,902,289 | 2/1990 | Yannas | 623/1 |
| 4,970,298 | 11/1990 | Silver et al. | 530/356 |
| 5,008,116 | 4/1991 | Cahn | 424/491 |

FOREIGN PATENT DOCUMENTS

| 0052001 | 5/1982 | European Pat. Off. . |
|---|---|---|

OTHER PUBLICATIONS

R. I. Freshney, *Culture of Animal Cells*, ch. 8, p. 65 (Alan R. Liss, Inc., New York, 1953).
J. Leighton, *Journal of the National Cancer Institute*, vol. 15, No. 2, pp. 275–293 (Oct. 1954).
J. Leighton et al., *Science*, vol. 155: pp. 1259–1261 (Mar. 1967).
I. V. Yannas and A. V. Tobolsky, *Nature*, vol. 215: pp. 509–510 (1967).
J. Folkam et al., *Cold Spring Harbor Conferences on Cell Proliferation*, vol. 1, pp. 833–842 (1974).
R. A. Messing and R. A. Oppermann, *Biotechnology and Bioengineering*, vol. 21: pp. 49–58 (1979).
I. V. Yannas and J. F. Burke, *Journal of Biomedical Materials Research*, vol. 14: pp. 65–81 (1980).
I. V. Yannas, et al., *Journal of Biomedical Materials Research*, vol. 14: pp. 107–132 (1980).
N. Dagalakis, et al., *Journal of Biomedical Materials Research*, vol. 14: pp. 511–528 (1980).

P. Gerhardt, et al., *Manual of Methods for General Bacteriology*, pp. 456–457 (1981).
J. L. Bomben, et al., *Cryobiology*, vol. 20: pp. 574–586 (1983).
J. Feder and W. R. Tolbert, *Scientific American*, vol. 248: pp. 36–43 (Jan. 1983).
M. W. Glacken, et al., *Annals N.Y. Academy of Sciences*, vol. 413: pp. 355–372 (1983).
J. L. Reichard–Brown and R. Akeson, *Developmental Biology*, vol. 413: pp. 304–316 (1983).
V. G. Edy, *Advances in Experimental Medicine and Biology*, vol. 172: pp. 169–178 (1984).
S. B. Karkare, et al., "Continuous Production of Monoclonal Antibodies by Chemostatic and Immobilized Hybridoma Culture", *Verax Corporation Publication*, TM 122, (Aug. 1984).
R. G. Duff, *Trends in Biotechnology*, vol. 3: 167–170 (1985).
F. Cahn et al., *192nd ACS National Meeting, Anaheim, California*, Sep. 7–12, 1986, *Abstracts of Papers*, abstract MBTD/106.
K. Nilsson et al. *Bio/Technology*, vol. 4, pp. 989–990 (Nov. 1986).
R. S. Cherry and E. T. Papoutsakis, *Bioprocess Engineering.*, vol. 1: pp. 29–41 (1986).
M. S. Croughan, et al., *Biotechnology and Bioengineering*, vol. 29: pp. 130–141 (1987).
K. Nilsson, et al., *Methods in Enzymology*, vol. 135: pp. 399–410 (1987).
S. T. Boyce, et al., *Journal of Biomedical Materials Research*, vol. 22: pp. 939–957 (1988).
M. S. Croughan, et al., *Biotechnology and Bioengineering*, vol. 32: pp. 975–982 (1988).
"CultiSpher-G" product brochure, (Percell Biolytica; Lund, Sweden; 1988).
R. M. Sutherland, *Science*, vol. 240: pp. 177–184 (1988).
I. V. Yannas, et al., *Proc. National Academy of Science*, vol. 86: pp. 933–937 (Feb. 1989).
I. V. Yannas, *Encyclopedia of Polymer Science and Engineering*, vol. 15, 2nd edition, pp. 317–334 (1989).
F. Cahn; *Tibtech* vol. 8: 131–136 (May 1990).
E. Adema et al., *Biopharm* (Jul./Aug. 1990).
Lim, *Biological Abstracts*, vol. 63, No. 9, pp. 4826–4827 1977.
"CultiSpher-G" Macroporous Gelatin Microcarrier product data bulletin (Percell Biolytica; Lund, Sweden).

*Primary Examiner*—Robert A. Wax
*Assistant Examiner*—K. Cochrane Carlson
*Attorney, Agent, or Firm*—Kalow, Springut & Bressler

[57] ABSTRACT

A porous particle having a generally isopycnic density with liquid growth medium, a sponge-like character and a diameter of less than 2 mm which is formed from a homogenous biologically compatible matrix is described. This particle is useful in various systems for culturing anchorage-dependent and -independent cells, and is adaptable to large scale tissue culture which permits harvesting of cell products. The method of making such a particle includes preparing a solution containing a biologically compatible material, forming droplets from the solution, freezing the droplets, drying the droplets by sublimation to form a particle, and crosslinking the biologically compatible material in the particle.

11 Claims, 8 Drawing Sheets

METHOD OF MAKING A POROUS MATRIX PARTICLE

BACKGROUND OF THE INVENTION

This application is a continuation-in-part of U.S. Ser. No. 682,645, filed Apr. 9, 1991, now abandoned, which is a continuation-in-part of U.S. Ser. No. 203,580, filed May 27, 1988, now abandoned, which in turn is a continuation of U.S. Ser. No. 688,630, filed Jan. 3, 1985, now abandoned; the contents of each are hereby incorporated by reference.

A process to make porous microcarriers or microsponges for tissue repair or immune stimulation must be capable of controlling particle size, shape, and internal average pore size. Particle size should be controlled between about 400–700 μm for microcarriers. Smaller size particles are useful for immunostimulatory applications. The particle should be highly spherical to provide good hydrodynamic properties and minimal attrition in stirred culture, and good deliverability by syringe in medical applications. Pore size should be controlled to allow for cell ingrowth and sufficient material strength.

Internal pore structure of the microcarrier particles is generated by ice crystallization during the freeze-forming step. Yannas in U.S. Pat. No. 4,522,753 teaches that the porosity of frozen collagen-GAG may be preserved by freeze-drying it followed by dehydrothermal crosslinking so that the pores do not collapse during subsequent re-hydration. For porous foams made in the form of a sheet, collagen-GAG is poured into a shallow pan and placed on the freeze-drier tray, which is chilled to a set temperature.

It is believed that dendritic spacing in the frozen collagen-GAG droplet determines average pore size in the resulting collagen-GAG droplet and pore size is dependent upon the freezing rate. Freeze-drying after the freeze-forming step maintains this pore structure. Thus, an empirical relationship between shelf temperature and mean pore size of the freeze dried foam can be determined to produce foams of defined pore size.

Bomben, et al. (*Cryobiology*, 20: 574–586, 1983) shows that the dendritic spacing of ice crystals in frozen solutions or fruit tissue was proportional to the inverse of the square root of the freezing rate (in ° K./min) as shown in their FIG. 20. Data indicates that spacings of 10–100 μm (suitable for wound dressings for animal cell growth) would be achieved at freezing rates between 0.1°–1° K./min. This indicates that to achieve pore sizes suitable for wound dressings or animal cell growth, it is necessary to achieve similar freezing rates for the particles as was achieved for solution poured into trays. However, the actual freezing rate cannot be calculated from empirical relationship of shelf temperature to pore size, nor can it be extended to the very different geometry of the small particle.

Berg, et al. (U.S. Pat. No. 4,837,285) recommends freezing particles in liquid nitrogen. Dean, et al. (U.S. Pat. No. 4,861,714) also recommends a "cryogenic" freezing bath, such as liquid nitrogen. Both methods allow no control over freezing rate or pore size. My experiments show that collagen-GAG suspensions frozen in liquid nitrogen have small pores (generally less than 2 μm) and an irregular shape. I have observed that the droplets of collagen-GAG droplets "sputter" near the surface of the liquid nitrogen, leading to clumping of the particles. U.S. Pat. No. 4,863,856, to Dean, et al. states that larger pores can be formed by subsequently annealing particles for several hours at −10° C. to −20° C., but a method to insure a spherical bead and avoid clumping is not disclosed.

I have discovered a rapid and practical process for producing spherical particles with controlled size and pores of desired average size, both at the surface of the particle and in the interior.

I have found that particles can be successfully frozen in a bath of immiscible liquid hydrocarbon maintained at a controlled temperature. By contrast, Dean suggests the use of ethanol (a miscible liquid). I have observed that the particles frozen in chilled ethanol have an irregular shape. Berg suggests a cooled organic solvent less than −20° C., such as hexane, chloroform, or methanol. However, methanol is a miscible solvent and is expected to have the similar properties to ethanol, giving rise to an irregular particle. Chloroform is denser than water and the frozen particles float to the surface and agglomerate with unfrozen droplets.

I have observed that it is important that the freezing bath have a specific gravity lower than that of ice, e.g. about 0.90. Liquid hydrocarbons, such as hexane or Isopar H (Exxon) (an isoduodecane mixture), are suitable immiscible liquids for the freezing bath. Ideal liquids have low toxicity and are have high flash point (or are non-flammable). By mixing a hydrocarbon with a high density liquid (such as 1,1,2 trichlorotrifluoroethane (CA 76-13-1) to achieve a specific gravity between 0.893 to 0.895 minimizes the velocity of the falling droplets in the freezing bath and allows freezing to be more complete before the particle reaches the bottom of the freezing bath. Preferably, the bath can be designed to have an upward flow of liquid at a velocity less than the Stokes velocity of the particles. This arrangement allows the freezing liquid to be temperature conditioned in a recirculating loop outside of the freezing bath.

When I froze collagen-GAG droplets in the immiscible liquids, hexane, or Isopar H, I obtained spherical particles. Immiscibility allows the surface tension of the aqueous droplet to create the spherical particle shape.

An ideal freezing liquid has a density below 0.90, is non-explosive and has low toxicity for safe manufacture, and immiscibility with water.

I discovered an empirical relationship between pore size and bath temperature. I also discovered that it was important to control the temperature of the collagen-GAG droplets at 0° C. (±0.25° C.) before they contact the freezing bath.

A satisfactory freezing bath must be deep enough so that particles are fully frozen before they reach the bottom of the bath; otherwise, particles will adhere and clump. For the Isopar H-trichlorotrifluoroethane mixture described above, the depth should be greater than 30 cm.

To grow anchorage-dependent animal cells in quantity, microcarriers (such as Cytodex 1, 2 or 3) are typically used. Solid microcarriers provide a surface area to support the growth of anchorage-dependent cells. These microcarriers are neutrally buoyant (hydrated density about 1.02–1.04) and about 150–200 μm in diameter, thus having a specific surface area of about 333 $cm^2$. Cell growth on solid microcarriers is limited by available surface area. The internal volume of a solid microcarrier occupies a major portion of the bed volume and is unavailable to cell growth, limiting cell concentration per unit of bed volume. When microcarriers are used in typical concentrations between 3 and 10% (v/v), the effective surface area is 10–30 $cm^2$; typical cell densities of $1.5 \times 10^5$ cells/$cm^2$ can yield up to about $4 \times 10^6$ cells/$cm^3$.

A serious drawback to solid microcarriers is the sensitivity of the cells growing on the outside of the bead to agitation. Cell damage may result from the interaction of a bead with a turbulent eddy, the collision of two microcarriers, or a microcarrier impacting with the impeller of other parts of the reactor (R.S. Cherry, and E. T. Papoutsakis, *Bioproc. Eng.*, 1: 29–41 (1986)). Croughan, et al., (*Biotechnol. Bioeng.*, 29: 130–141 (1987)) shows that at low microcarrier concentrations, net cell growth is reduced when the length of the smallest eddies, as measured by the Kolmogorov radius, approaches the diameter of the microcarriers. The small eddies apparently are able to dissipate their energy on the cells at the surface of the bead. A second mechanism of cell damage is due to bead-bead interactions and increases with the bead concentration to the second power; this mechanism is the dominant cause of cell death at high microcarrier concentrations (M.S. Croughan, et al., *Biotechnol. Bioeng.*, 32:975–982 (1988)). These factors limit culture density, practical volume of the culture, and culture longevity.

In addition, some cells fail to attach or grow on microcarriers, and in other cases confluent cell layers spontaneously detach from the microcarriers. In an attempt to improve attachment and growth properties of microcarriers, different surface chemistries have been tried: Cytodex 1 has a surface of charge-optimized DEAE-dextran; other microcarriers have been made with surfaces of denatured collagen (gelatin), polystyrene, or glass. Since the diameters of these different microcarriers are similar (varying from about 120 to 230 μm), as are the hydrated densities (varying from about 1.02 to 1.04 g/cm$^3$), all of these materials have similar hydrodynamic properties. Thus, none of these modifications can overcome the fundamental hydrodynamic limitations of the microcarrier, noted above.

These modifications of microcarrier surface chemistry have been of limited additional utility, and frequently are much more expensive than Cytodex microcarriers. Cytodex microcarriers provide surface areas from 2700 to 3400 cm$^2$/g, but various plastic, glass and gelatin-coated microcarriers provide much less surface area per gram (250–500 cm$^2$/g). This substantial difference is due to the large amount of water absorbed by Cytodex upon hydration, yielding a bed volume of 14–18 cm$^3$/g (some microcarriers are ten times more expensive than Cytodex per cm$^2$ of surface area.)

I have discovered that hydrodynamic and other limitations of microcarriers may be overcome by using a porous microcarrier in which cells grow with minimal surface exposure to detrimental hydrodynamic stress. A porous microcarrier is a preformed particle with porous internal structure into which animal cells can be grown and maintained in suspension in culture medium.

Furthermore, by making the porous microcarrier beads from freeze-dried collagen-glycosaminoglycan (GAG) crosslinked copolymer (U.S. Pat. Nos. 4,522,753, 4,448,718, and 4,280,954), very high void volumes and controlled pore structures with very high internal surface areas can be achieved which maximize the cell densities in the microcarrier. Because this material is made from components of the extracellular matrix of animal cells, it is particularly suitable for attachment and growth of anchorage-dependent animal cells. I have found that cells grown in porous microcarriers are not subject to cell detachment during culture maturation. A further unexpected advantage of my approach, is that the particles can be used to entrap anchorage-independent cells at high density in the microcarrier; this property may be utilized to increase cell density in the culture as well as to help retain cells when are used in a perfusion culture system.

With the porous microcarrier, cells occupy the internal void volume of the particles. Since collagen-GAG microcarriers typically have greater than 90% void volume (often 99%) and controlled pore size, essentially the entire internal volume is available for cell growth. Generally, the limits of cell growth are determined by this internal volume, and not by either exterior or interior surface area. I have found that cells such as the monkey kidney cells line CV-1 and the Chinese hamster ovary cell line CHO (which is often used in recombinant DNA protein expression) can grow to very high densities in the collagen-GAG microcarriers, occupying greater than 90% of the void volume; even VERO (a monkey kidney cell line used in vaccine manufacture) cells, which form monolayers which do not completely fill in the voids, can occupy more than 50% of the microcarrier volume. In comparison, at typical cell densities of 1.5×10$^5$/cm$^2$, solid microcarriers only support between 0.05 and 0.2 ml of cells per ml of microcarrier bead volume (assuming cell diameters of 12–20 μm). Accordingly, porous microcarriers can support 2½ to 18 times the volume of cells per unit of microcarrier volume. Generally, the amount of biomass (roughly proportional to volume) in a culture determines its productivity for producing a metabolic product.

Previous collagen-based porous materials used for cell culture (Leighton, J, et al., *Science*, p1261 (1967)) apparently did not have the stable controlled pore size made possible by the high degree of crosslinking and preservation of pore structure. The Leighton collagen sponge collapsed during in cell culture, requiring a more complex method of collagen-coated cellulose to prevent pore collapse. Moreover, these materials were fabricated in the form of thin sheets, and not in the form of porous particles capable of being used in microcarrier suspension culture systems. Some other porous materials have been used to grow microbial cells (U.S. Pat. No. 4,503,150) and plant cells (Childs, A. F., et al., EP 0 052 001 (1981)). However, these materials are also not appropriate for animal cell suspension culture because they were not made from materials with surface chemistries designed for animal cell attachment and spreading, and had inappropriate pore size and overall size.

Previous attempts to provide a protected environment which would allow animal cells to be grown in large volume or density had serious disadvantages. Culture in porous microcarriers is superior to encapsulation (U.S. No. Pat. 4,409,331; R. G. Duff, *Trends Biotechnol*, 3: 167–170 (1985)) and gel entrapment (K. Nilsson, et al., *Meth. Enzymol.*, 135: 399–410 (1987)) because these methods require the cell inoculum to be combined with gelling agents and formed into droplets of controlled size and be gelled and/or encapsulated. These steps require specialized apparatus and must be carried out entirely under sterile conditions. Furthermore, gels and capsules are soft or fragile and cannot withstand prolonged vigorous agitation. Further, gel and encapsulation methods are generally suitable only for anchorage-independent cells because the gel or liquid interior does not provide a suitable surface for cell attachment. High calcium concentrations needed to gel the alginate used in most encapsulation and entrapment methods can be toxic to many cell lines.

U.S. Pat. No. 4,743,545 to Torobin, entraps cells in rigid hollow porous microspheres. After introduction of the cells, the porous shell is sealed (e.g., with a gel) so as to retain the cells in the microspheres. This approach is distinguished from the subject invention by the presence of a single interior void and need for an immobilizing gel or membrane to retain the cells. Torobin's approach is thus not suitable for culturing of anchorage-dependent cells and has the disadvantage of requiring the entrance pores to be sealed after inoculation.

Like encapsulation and gel entrapment, porous microcarriers can provide protection from the effects of shear and air-liquid interfaces in vigorously agitated cultures. They have the important advantage of simplicity because inoculation of the preformed material can take place directly in a bioreactor without additional hardware, as with the solid microcarriers, making them practical for use in industrial processes. I have found that crosslinked collagen-GAG copolymers form strong porous microcarriers capable of withstanding vigorous agitation and can be utilized for both anchorage-dependent and anchorage-independent cells.

The increase in cell density per unit of microcarrier bed volume and the ability of the matrix to protect cells against shear in agitated cultures contribute to an ability of porous microcarriers to support much higher cell densities in suspension cultures. In addition to the increase the mass of cells per unit microcarrier bead volume, further increases in cell density may be achieved by increasing the amount of microcarrier bed volume in the reactor; more vigorous agitation can be used to maintain the microcarrier slurry in suspension because of the shear protection of the porous microcarriers. Furthermore, increased agitation can achieve a higher mass transfer coefficient ($k_L a$) of oxygen into the culture medium necessary to maintain cell viability at a higher cell density. Optimal utilization of porous microcarrier properties are thus achieved in reactor systems capable of vigorous agitation and efficient oxygenation.

SUMMARY OF THE INVENTION

The invention provides a porous matrix particle having a generally isopycnic density with respect to liquid growth medium, a sponge-like character and a diameter of less than about 2 millimeters. The particle consists essentially of a homogeneous biologically compatible matrix having a multiplicity of voids therein. The voids represent at least 10% of the total volume of the particle and are connected to pores of less than 100 µm in diameter which connect the voids to the exterior of the particle (hereinafter these particles are referred to as the preferred particles).

The preferred particles used in the invention may utilize a biologically compatible material selected from the group consisting of collagen, urethane, cellulose, saturated polyester, poly(ethylene terephthalate), polyamide, poly(hexamethylene adipamide), poly (2-hydroxyethyl methylacrylate), and diatomaceous earth. However, the preferred material comprises collagen. Typically, the preferred particle is capable of supporting more than 2.5 times the volume of animal cells that can be cultured on an equal bed volume of solid DEAE-dextran microcarriers of 180 µm diameter.

The subject also provides a method of making a porous matrix particle having a generally isopycnic density with liquid growth medium, a sponge-like character and a diameter of less than about 2 millimeters. The particle consists essentially of a homogeneous biologically compatible matrix having a multiplicity of voids therein, the voids representing at least 10% of the total volume of the particle. The voids are connected to pores of less than 100 micrometers in diameter which connect the voids to the exterior of the particle. The method comprises: preparing a solution containing a biologically compatible material; forming droplets from the solution; freezing the droplets in a temperature controlled fluid hydrocarbon; drying the frozen droplets by sublimation to form a particle; and crosslinking the biologically compatible material in the particle.

Also provided is a system of culturing anchorage dependent animal cells. This comprises: a plurality of the preferred particles, animal cells installed in the voids of the particles subsequent to the particles' formation, liquid growth medium substantially surrounding the particles, means for supplying oxygen to the cells, and means for agitating the medium so as to maintain the particles in suspension within the medium.

Preferably, the system of culturing animal cells and producing cell products is capable of supporting more than 2.5 times the volume of animal cells that can be cultured on an equal bed volume of solid DEAE-dextran microcarriers of 180 µm diameter.

The invention also teaches a method of culturing animal cells and harvesting a cell product which comprises: inoculating the preferred particle with animal cells, oxygenating the medium, agitating the medium to maintain the particle in suspension, adding medium at a controlled rate so as to displace medium which has been exposed to the cells, collecting the displaced medium, and harvesting the desired cell product from the displaced medium.

A system for culturing anchorage independent animal cells is also provided. This system comprises a plurality of the preferred particles, animal cells capable of entering the voids of the particles, liquid growth medium substantially surrounding the particles, means for supplying oxygen to the cells, and means for agitating the medium so as to maintain the particles in suspension within the medium. By selecting a collagen having a transitional temperature only slightly above the body temperature of the animal form which the cells were obtained, it is possible to shrink the collagen after the cells have been introduced into the voids.

DETAILED DESCRIPTION OF THE INVENTION

Figure 1:
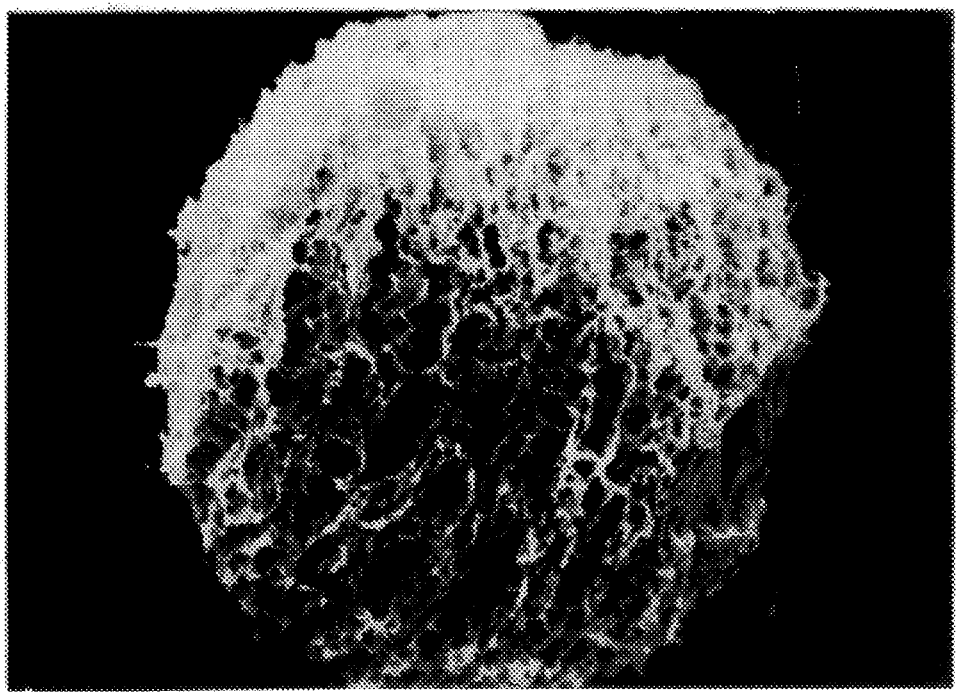
FIG. 1: Scanning electron micrograph (75× magnification) of a porous microcarrier particle made of freeze-dried collagen-glycosaminoglycan crosslinked copolymer.

Optimal physical properties for porous particles, such as particle size, pore size, and particle density are determined in light of requirements for nutrient exchange between the medium and cells. A critical factor is limited oxygen solubility in aqueous solutions which require continual replenishment of oxygen in the culture medium surrounding the particles.

Porous microcarriers used in spinner flask, stirred tank, or air lift fermenter suspension culture systems should be near neutral buoyancy to be suspended at reasonable agitation rates, densities between about 1.00 g/cm$^3$ and about 1.04 g/cm$^3$ are most appropriate. Since neutrally buoyant particles flow with the flow of the medium, the particles and medium form a slurry which must be oxygenated. Oxygenation methods used in microcarrier culture include large area membranes and proprietary bioreactor configurations (such as those using screens to separate the microcarriers from the aeration system); sparging may be possible for porous microcarriers since they can protect cells from direct contact with the air-liquid interfaces.

Optimal microcarrier particle size represents a compromise between opposing functions. For protection of cells, the maximum ratio of internal volume to surface area occurs at large radii. But since on damage to the cells growing on the surface of the particles occurs when the particle size approaches the Kolmogorov radius of the turbulent fluid, surface cells on large particles are especially susceptible.

Large size also increases the path for diffusion of nutrients to a particle's interior, which may lead to anoxia for interior cells. If cells fail to grow into the center of the particle, there may be little effect on overall performance (since a sphere includes only 12.5% of its volume in the interior half of its radius). I have observed such a self-limitation of cell density in the interior of large porous microcarrier particles (about 1.5 mm diameter) when VERO cells are grown on them. A greater problem occurs when cells grow into the interior and later die, because soluble necrotic cell products may diffuse out of the microcarrier, contaminate the culture medium, and make purification of an extracellular product more difficult. Glacken, et al., *Ann. N.Y. Acad. Sci.*, 413: 355 (1983), computed that a microcapsule would be nutrient limited at a diameter of about 170 µm. Experimental evidence by Sutherland, *Science*, 240: 177–184 (1988), shows that for tumor spheroids grown under optimal nutrient and oxygen conditions the distance from the spheroid periphery to the region at which necrosis occurs varies from about 100 to 220 µm, at cell packing densities of 35 to 55%. Measurement of oxygen partial pressure with oxygen microelectrodes inserted into the spheroids showed steep gradients of oxygen near the periphery and very low concentrations beyond about 100 µm from the surface.

These observations indicate that diameters between 200 µm and 440 µm should be compatible with high cell viability in the particle interior. However, my experiments show that unexpectedly high cell densities (approaching 100% occupancy of the particle voids) can be obtained in particles of 400–900 µm in diameter without evidence of necrosis (determined by histological sections of the porous microcarriers).

Size dispersion of particles is an additional consideration. My experiments show that even irregular particles made by comminuting a sheet of porous collagen-GAG to particles about 300–500 µm and pore sizes of 20, 35 or 50 µm can be used in spinner flasks to culture CHO cells (which can grow either anchorage-independent or anchorage-dependent), anchorage-dependent human fibroblast cell line MRC-5, and anchorage-independent hybridoma cells when suspended in spinner flasks at low concentrations of particles (about 3% bed volume). However, beaded particles with a uniform size distribution are ideal for consistent hydrodynamic and mass transfer properties at high particle concentrations and large reactor volumes. I have obtained satisfactory results with beaded particles having a wide size distribution (e.g., typically between about 400 and 900 µm).

Void volume determines maximum internal cell density. Higher void volume is desirable because it increases both the number of cells which can be grown per gram of microcarriers and per liter of microcarrier bed volume. Freeze-dried collagen-GAG has very high void volumes of greater than 90% (as much as 99%).

In freeze dried collagen-GAG, which I have used for porous microcarriers, there are wide pore size dispersions; thus they are characterized by a statistical pore size distribution. Average pore size can be measured on micrographic sections by stereological procedures (for example, by dividing the length of a test line by the number of its intersections with the pore walls). The most fundamental consideration for pore size is that the majority of pores should be larger than the cell diameter so that cells can penetrate into the interior. For most anchorage dependent cells, pores larger than about 20 µm are adequate. At small average pore diameters cells may be excluded from a significant fraction of void volume. Pore size must be significantly smaller than the particle size if the particle is to have mechanical integrity and, indeed, have an "interior" at all. In my experiments, when a sheet of porous collagen-GAG with average pore size greater than 100 µm is comminuted to particle sizes about 300–500 µm, a granular particle form was not evident. However, when the average pore size was 50 µm or less, a defined particle resulted. While there is presently no quantitative theory to predict maximum pore size, a maximum average pore diameter less than about 20% of the particle diameter seems reasonable.

For microbial cells entrapped in porous glass, an optimal pore diameter of one to five times the cell diameter exists R.A. Messing, et al., *Biotechnol. Bioeng.*, 21: 49–58 (1979)). For animal cells, optimal pore diameter is expected to depend on cell type, since cells differ in diameter, ability to form multilayers, ability to spread into small pores, etc. At an average pore size larger than twice cell diameter, highly anchorage dependent cells which grow to confluence without multilayering will leave an interior void space. Maintenance of interior void space in a mature culture can have several consequences: (i) the cells do not completely occupy the void volume, and (ii) channels are present which may permit convective medium flow. Either effect may increase optimum particle diameter based on the above considerations concerning the balance between protection and nutrient transfer. I have discovered that two anchorage dependent cells which do not multilayer in flasks or solid microcarriers behave differently in porous microcarriers: VERO grows as a monolayer leaving internal voids, whereas CV-1 will completely fill the void space of the microcarriers. The limiting cell density and presence of channels will need to be determined experimentally for particular cell lines and may also be dependent on culture medium.

Optimal microcarrier chemical properties will vary according to the requirements of the cells to be grown. For anchorage independent cells, only physical entrapment of the cells are required. Immortal anchorage dependent cell lines generally can be cultured on a variety of synthetic or natural surfaces. The surface should support both attachment and spreading of the cells after inoculation, and support cell growth. A controlled density of ionic charge is necessary to support cell attachment. Further development of attachment and the spreading of cells depends on the presence of adhesion macromolecules or their synthesis by the cells. The rate of these processes is generally slower than the rate of initial attachment on particles of optimal ionic charge; frequently there can be slower attachment to gelatin or collagen microcarriers than to charge-optimized DEAE-dextran based microcarriers.

Primary animal cells and some cell lines are more fastidious and show additional requirements. Natural biomaterials such as gelatin, native collagen, or and/or attachment factors such as fibronectin or laminin may be necessary to support attachment and growth. The maintenance of differentiated cell function in primary cells poses the strictest requirement for support surface chemistry. Maintenance of differentiation in culture may require specific biochemicals derived from the extracellular matrix such as native collagens, glycosaminoglycans, attachment factors, or mixtures of these.

For porous microcarriers, an absence of leachable cytotoxic components is an obvious requirement. Additionally, leachable contaminants (especially pyrogens) which may find their way into products derived from the culture are undesirable. Autoclavability is a desirable property to simplify bioreactor loading procedures. Non-autoclavable materials such as collagen and collagen-GAG need to be pre-sterilized; I have found that crosslinking with aqueous glutaraldehyde or dehydrothermal treatment of dry collagen-GAG at 105° C. for 24 hours or more at about 100 mtorr or less results in a functionally sterile product.

For applications requiring recovery of viable cells from the microcarriers, the ability to dissolve the microcarrier to release the cells is needed. Collagen and collagen-GAG can be dissolved with collagenase in the presence of divalent cations. I have observed the release of CHO and anchorage-independent cells after collagenase treatment, but with some cells, such as CV-1, which have grown to a dense mass which fills the voids of the collagen-GAG particle, little disaggregation of the cell mass is seen after 1–2 hours of collagenase treatment.

The collagen-GAG crosslinked graft copolymer chemistry which I have used to make porous microcarriers was first developed as a wound dressing capable of aiding the regeneration of the dermis, as shown in clinical trials (I.V. Yannas, et al., *Proc. Nat. Acad. Sci. USA*, 86: 933–937, (1989)). The materials science and chemistry of these materials has been thoroughly described (I.V. Yannas, and Burke, J. F., *J. Biomed. Mater. Res.*, 14: 65–81 (1980); I. V. Yannas, et al. *Biomed. Mater. Res.*, 14: 107–131 (1980); Dagalakis, N., Flink, J., Stasikelis, P., and I. V. Yannas, *J. Biomed. Mater. Res.*, 14, 511–528 (1980)). However, this material was not available in particulate form, nor had it been considered or evaluated as a substrate for in vitro cell culture.

Collagen-GAG chemistry has several advantages over native collagen which may make it preferable for certain cell culture applications: (i) it is more resistant to collagenase degradation and (ii) has improved mechanical properties. For porous microcarriers, the very high void volume allows cells to colonize nearly the entire volume of the particles so that the highest cell concentrations per liter of bed volume are possible. The high void volume fraction insures that the hydrated material is very nearly isopycnic with respect to the medium, so that it can be easily kept in suspension.

I have developed methods to form the freeze-dried collagen-GAG material into beaded particles of defined pore size (FIG. 1) and appropriate size. These particles do not undergo significant size change upon rehydration in dilute acid (0.05M acetic acid), but in phosphate buffered saline (PBS) a small volumetric shrinkage of about 20% may be observed. Accordingly, pore size developed during the freeze-drying step is also preserved upon rehydration. Furthermore, these particles maintain their form after prolonged cell culture, which is economically important, because a major manufacturing expense comes from removing water during the freeze-drying step itself (about one gram of water must be removed per ml of particle void volume). If a particle collapses on rehydration, the cell culture capacity per gram of water removed during freeze-drying is correspondingly reduced. The particles produced by my process preferably have diameters from about 400–900 µm, estimated hydrated density of about 1.002 g/cm$^3$, pore sizes of about 20–80 µm, and void volume of about 99%. The bed volume is about 250 ml/g, which can theoretically culture up to about 170 ml of cells/g of dry weight. The volume/surface ratio is about 200 cm. The processing steps do not denature collagen, as triple helical content is close to 100% as determined by electron microscopy and by mid- and far- infrared spectroscopy (I. V. Yannas, *Encyclopedia of Polymer Science and Engineering*, Vol. 15, 2nd edition, pp. 317–334), and the material is stabilized so that the highly porous structure does not collapse upon rehydration. I have confirmed by FTIR spectroscopy that the detail and peak-height of the conformation-sensitive band at 1235 cm$^{-1}$ is preserved in the finished microcarrier particles produced by my process. The microcarrier product can be shipped in a dry and sterile form in which it is not sensitive during transport and storage to freezing temperatures in Winter or hot Summer weather.

Basic processing of collagen-GAG microcarriers begins preferably with milled collagen prepared from limed bovine hide, such as Semed F from Semex Medical. Such collagen from limed hide is capable of forming a precipitate when GAG is added to a blended solution in dilute acid, as described below. The dry collagen (the assumed moisture content is 10%) is added to 0.05M acetic acid to make a 0.55% (w/v) suspension (the range of collagen concentration can be between about 0.25% and 1%, but high viscosity reached during blending makes collagen concentrations above about 0.5% difficult to achieve). The volume of the 0.55% suspension is 90% of the final volume.

I have found that collagen obtained from fresh wet-milled bovine hide, and which does not form a GAG precipitate, will form a GAG precipitate after treatment with a strong base, using the following procedure:

A. Comminuted bovine hide from fresh hide is obtained in a 0.5M acetic acid suspension at about 5–10 mg of collagen/ml.

B. The suspension is neutralized by adding 0.5 liter of 1M sodium acetate per liter of collagen and stirred for an hour.

C. The suspension is vacuum deaerated, which causes the collagen to rise to the surface. The liquid is decanted from the bottom.

D. Deionized water is added to restore the 1.5 liter volume. The mixture is stirred for one hour.

E. Wash steps C–D are repeated (wash 2).

F. The suspension is vacuum deaerated, and the wash liquid is decanted from the bottom.

G. The washed collagen is suspended in 1 liter total volume of water per liter of original volume in water.

H. 1M NaOH is added to yield a final concentration of 0.05M; the mixture stirred for 8–12 hours at room temperature.

I. The mixture is neutralized by adding acetic acid to form a 0.1M final concentration.

J. The collagen is washed three times with deionized water following the procedure in steps C–D.

K. The suspension is vacuum deaerated, and the wash liquid is decanted from the bottom.

L. The collagen is resuspended in about 300 ml of water per liter of original volume.

M. 1M acetic acid is added to make a final concentration of 0.05M.

N. The suspension is briefly homogenized with a blender, and samples are taken for dry weight determination.

O. Additional 0.05M acetic acid is added to make a final collagen concentration of about 0.55% (w/v).

Whether the limed collagen or treated collagen is used, the 0.55% suspension of collagen in 0.05M acetic acid is further treated as follows:

A. The suspension is thoroughly blended for about 0.5 hours using an IKA T50 blender at about 5,000 rpm with a G45G generator or a W65SK generator at 10,000 rpm. For maintenance of the temperature during blending below about 20° C., the blending is carried out in a stainless steel vessel in an ice-water bath. The blending can be monitored by phase-contrast microscopy at 100–200×magnification for disaggregation of the large fiber bundles and the appearance of a uniform ground of fine fibers. With this equipment, batches between about 0.5 and about 5 liters can be processed.

B. A solution of GAG equal to 10% of the final volume of the solution, usually chondroitin-6-$SO_4$, is then slowly added over a 5–15 min period during blending, forming a co-precipitate. The final collagen concentration is typically 0.5% (w/v) and typically the GAG concentration is 8% (w/w) relative to the collagen. To obtain the 8% (w/w) final GAG concentration relative to collagen, a 4 g/l GAG solution is used in this step.

C. The collagen-GAG suspension prefiltered by passing it through a filter screen with 0.008" (0.20 mm) circular holes to remove particles from the collagen-GAG feed.

D. The solution is deaerated by application of vacuum.

E. The suspension is formed into droplets in the 400–900 μm average diameter range by pumping through a 22 gauge cannulas in a spray head at 0° C. at a controlled flow rate of about 30 ml/min. The cannulas tip is surrounded by an annular space through which an atomizing air flow is maintained. The size of the droplets can be controlled by the following parameters: orifice diameter, flowrate of collagen-GAG through the orifice, flow rate of gas (nitrogen or air) past the orifice (through annular space surrounding needle). The particle size also depends on the viscosity and surface tension of the collagen-GAG mixture.

F. The droplets freeze after they impact and fall through the cold collection fluid (e.g., hexane). A collection bath temperature of about −9° C. produces a useful pore size distribution of about 20–80 μm. The temperature should be maintained with a deviation of less than ±5° C. The particles collect in a pile at the bottom of the vertical collection vessel, which should be more than 20 cm deep. The freezing process is completed and the particles remain frozen as they collect at the bottom of the collection vessel. While hexane is a satisfactory freezing solution, it is very flammable. A preferable freezing material is less volatile, such as Isopar H (Exxon). By mixing Isopar H with 1,1,2 trichlorotrifluoroethane (CA 76-13-1) to a specific gravity between about 0.893 and 0.895 g/$cm^3$, the sinking of the droplets can be retarded so that they are more completely frozen by the time they reach the bottom of the vessel. Other immiscible hydrocarbons may also be used for freezing.

G. After completing a freeze-forming run, the frozen particles are transferred to rectangular pans about 2 inches deep and excess freezing solution is decanted. The heat transfer during freeze drying is improved by constructing the pans with fins about 1 inch apart.

H. The pans are placed in a freeze-dryer which is set-up to operate at a pressure of approximately 100 mtorr. The temperature of the sublimation front at this pressure is approximately −40° C. The temperature of the freeze-dryer shelves is maintained at −40° C. to −50° C. while the frozen particles are being loaded into the freeze-dryer.

I. Once the particles are loaded and a vacuum has been established, the residual solvent in the evaporates and is trapped in the condenser as a liquid; if hexane is used, it is drained off before the final freeze-drying step.

J. Once all of the solvent has been removed, the shelf temperature is gradually increased to 0° C. where it is maintained throughout the freeze-drying run. When hexane is used, a vacuum of 100 mtorr cannot be sustained in the freeze-dryer if any of the hexane has been introduced into the vacuum system; in this case a vacuum of approximately 300 mtorr is obtained during the freeze-drying process. This reduces the maximum allowable driving that can be obtained by using a shelf temperature of 0° C. Heat from the 0° C. freeze-dryer shelves is conducted to the collagen-GAG particles and supplies the heat needed to sublime the ice.

Figure 9:
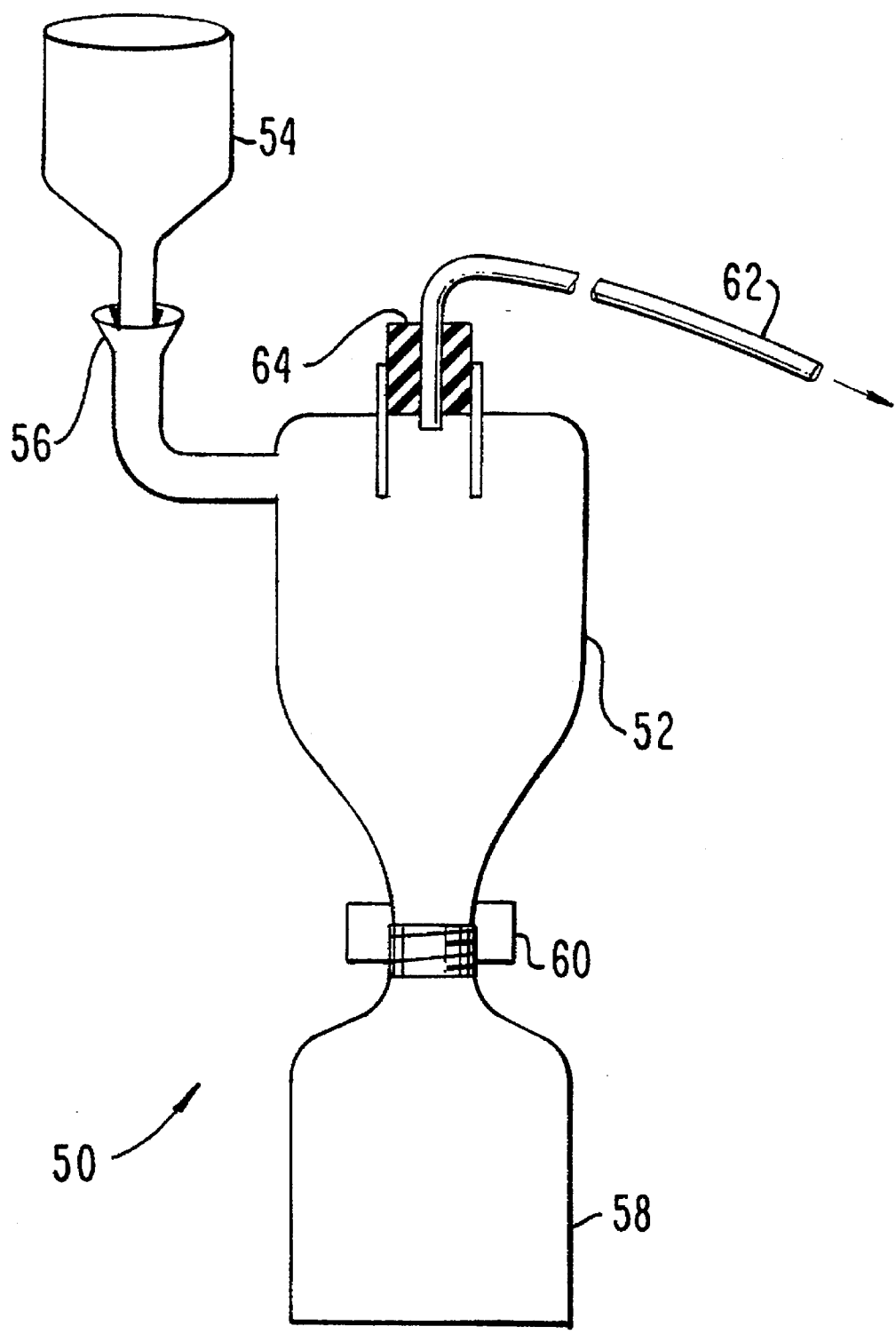
FIG. 9: Representation of a cyclone separator.

K. After a material is freeze-dried it is transferred to bottles using the vacuum operated cyclone separator (see, FIG. 9).

L. The bottled microcarriers are subjected to a vapor glutaraldehyde crosslinking process (see, U.S. Pat. No. 4,448,718):

1. The bottles are placed in a vacuum oven at room temperature of about 25° C.
2. The oven is evacuated, and nitrogen is introduced through a gas generator which sparges the gas through a 25% glutaraldehyde solution at room temperature.
3. After 30 min, the gas is evacuated from the oven with an aspirator and air introduced again.

M. The bottles are loosely capped, placed in a vacuum oven at 105° C. and evacuated to about 50–100 mtorr, and maintained for 1 to 5 days (typically, 1 day); the thorough dehydration (I. V. Yannas, et al., *Nature*, 215: 509–510 (1967)) crosslinks both the collagen and GAG.

N. Air is introduced through a sterilizing filter, and the bottles are tightly capped after they cool.

I have found that the microcarriers prepared by this procedure are sometimes difficult to rehydrate. A satisfactory procedure is to rehydrate in a small volume of 50–95% ethanol (typically 70%). About 10 volumes of sterile PBS is added, and after the microcarriers settle, the PBS is decanted; the wash is repeated and the microcarriers are ready to inoculate. A preferred procedure which required less ethanol and less washing is to add about 1 ml of 95% ethanol per 50 ml of bed volume of microcarriers and recap the bottle. After several (e.g. four) days, PBS or culture medium can be added to the microcarriers; any residual air is expelled within a few hours. The microcarriers can then be diluted to the working volume or optionally washed to remove ethanol.

After rehydration, the collagen-GAG microcarriers should not be exposed to high temperatures to avoid denaturation of the native collagen structure. This temperature is above 40° C. (the approximate denaturation temperature for uncrosslinked, soluble bovine collagen) since it is highly crosslinked. I have prepared beds of about 5 ml of microcarrier prototypes in PBS in 15 ml conical centrifuge tubes and incubated them at various temperatures in a circulating water bath. At 40° C. no shrinkage of the bed occurred. When the temperature was raised to 44° C., the bed contracted by about half within 5 minutes in several test lots. In all lots, the bed contracted when incubated at 50° C. (I believe that the differences in shrinking temperature between lots was due to variability in the degree of crosslinking). Therefore, this material should not be autoclaved. Storage of hydrated microcarriers under refrigeration is for periods of up to a month or two does not seem to harm them; the hydrated microcarriers should not be frozen to avoid ice formation from disrupting the structure.

Microcarriers can be used with conventional animal cell culture medium; however, high serum concentrations (above 5%) may cause the microcarriers to clump.

My experiments using 125 ml spinner flasks (Corning) show that the inoculation efficiency for certain some cells onto the porous microcarriers may be sensitive to stirring rate. Very slow stirring (e.g., 10 rpm) or intermittent stirring used for the first 2–8 hours after inoculation produce a highly satisfactory result. I have found also that the progress of inoculation can be monitored conveniently by staining the microcarriers with crystal violet fixative stain (0.5% crystal violet in 40% ethanol) to observe the attachment of cells to surface during inoculation. After about one minute of staining at room temperature, the excess stain is washed with at least three changes of PBS.

Crystal violet stain is useful in examining the inoculation of porous microcarriers; after cell growth has occurred, cells in the interior may be visualized by histological sectioning procedures. For histology, approximately 2 ml aliquots of cell cultures were withdrawn with 10 ml pipettes and the microcarriers are allowed to settle in 15 ml plastic centrifuge tubes. Excess medium is aspirated and about 5 ml of a 10% (v/v) dilution in PBS of 40% formaldehyde is added. Samples are stored under refrigeration before being sent for commercial histological processing.

The collagen-GAG mixture (0.5% w/v in 0.5M acetic acid) was formed into droplets (ranging in size from 300–500 µm) using a freeze-forming apparatus. Flowrate of collagen-GAG to the freeze-forming apparatus was controlled by the pressure in the headspace over the feed bottle. Droplets of the collagen-GAG mixture form as the mixture is forced through the needle orifice. The size of the droplets was controlled by the combined influence of the following parameters:

orifice diameter, flowrate of collagen-GAG through the orifice, flowrate of gas (nitrogen or air) past the orifice (through annular space surrounding needle), the viscosity of the collagen-GAG mixture, and the surface tension of the collagen-GAG mixture.

The droplets froze after impacting and falling through the cold collection fluid (n-hexane). Droplets were at least partially frozen (the outer shell of the particle freezes first) by the time they reached the bottom of the collection vessel, where they collect in a pile. Freezing completed, the particles remain frozen at the bottom of the collection vessel.

To optimize the pore structure of the particles, two parameters were varied:

I. The set point temperature for the collagen-GAG in the orifice assembly, which was varied between −1.0° C. This temperature was controlled by monitoring the collagen-GAG temperature and manually controlling the flowrate of a refrigerated coolant (ethanol/water solution) through the jacket of the orifice assembly.

II. The setpoint temperature for the hexane freezing bath was maintained between −45° C. and −5° C. Liquid nitrogen was also evaluated as a freezing fluid.

In these experiments, I was able to maintain the temperature near the surface of the bath within this range of about ±2° C., but was unable to effectively control the temperature throughout the entire volume of the collection vessel. Temperature at the bottom of the collection vessel steadily increased during the run, probably because of poor heat transfer in the bottom of the collection vessel and because of the heat released by the freezing process.

After completing a freeze-forming run, frozen particles were transferred into rectangular glass flasks. A portion of the cold collection fluid was transferred along with the particles into the flasks, which were stored in a freezer (−20° C.) or on dry ice until freeze-drying.

Liquid hexane was drained from the freeze-drying flasks before loading into the freeze-dryer. The depth of this layer of particles is controlled to maximize freeze-dryer loading while providing for adequate mass and heat transfer. I have typically limited the depth of the particles in the flasks to approximately 1 cm.

The freeze-dryer operates at a pressure of approximately 100 mtorr (0.1 mm Hg, or 29.89" Hg of vacuum). The temperature of the sublimation front at this pressure is approximately −40° C. (−40° F.). The temperature of the freeze-dryer shelves is maintained at −40° C. to −50° C. while frozen particles are loaded into the freeze-dryer. Once the particles are loaded and a vacuum established, residual hexane in the freeze-drying flasks evaporates and is trapped in the condenser as a liquid. (My condenser is not cold enough to freeze hexane; as a result, I must drain hexane from the condenser before pulling a good vacuum).

After the hexane has been removed, shelf temperature is gradually increased to 0° C. and maintained throughout the freeze-drying run. I typically achieve and maintain a vacuum of approximately 300 mtorr during the freeze-drying process. As described above, this reduces maximum allowable drying that can be obtained by using a shelf temperature of 0° C. Heat from 0° C. freeze-dryer shelves is conducted to the collagen-GAG particles and supplies heat to sublime the ice.

Pore size distributions of freeze dried particles were examined by Scanning Electron Microscopy. Both the exterior surface and the interior of particles cut by a razor were photographed. Generally, interior pores are larger than surface pores, presumably because the freezing rate in the interior is slower than at the particle surface due to a longer heat transfer pathway. The approximate average pore size was measured by stereology by dividing the length (in µm) of a calibrated line placed over the photograph of the surface or interior by the number of times collagen-GAG fibers or sheets crossed the line.

Two experiments were conducted to determine the relationship of pore size to freezing bath and orifice temperature. In the first experiment, the orifice temperature was maintained at −1.0° C. and the freezing bath temperature was maintained at −40° C., −30° C., −15° C. and −10° C. A bath of liquid nitrogen was also tested. The following data were obtained:

| Bath °C. | Orifice °C. | Mean surface pore size (µm) | Mean interior pore size (µm) |
|---|---|---|---|
| −10 | −1 | 7 | 37 |
| −15 | −1 | 17 | 33 |
| −30 | −1 | 2.5 | missing |
| −40 | −1 | 1.2 | 6 |
| Liquid N$_2$ | −1 | 1.8 | 25 |

From this experiment, it appears that optimal mean pore size at the surface, at least 10 µm to allow entry of cells, is achieved at −15° C. or above. Also, the anomalous result at −10° C. required that the experiment be replicated and suggested that an additional variable could affect results.

Therefore, in the second experiment, a 2×2 factorial design with centerpoint (which was replicated) was used; both orifice temperature and bath temperature were varied. The centerpoint was −10° C.

| Bath °C. | Orifice °C. | Mean surface pore size (µm) | Mean interior Pore size (µm) |
|---|---|---|---|
| −5 | −0.5 | low surface porosity | 37 |
| −5 | +0.5 | low surface porosity | 42 |
| −9 | 0 | 11 | 33 |
| −9 | 0 | 18 | 46 |
| −15 | −0.5 | 7 | 10 |
| −15 | +0.5 | 6 | 24 |

From this experiment, I determined optimum conditions for producing a pore size which admits cells into the interior to be obtainable at about −9° C. with an orifice temperature of about 0° C. Subsequent experiments with these settings, with Isopar H in the freezing bath instead of hexane, consistently resulted in similar surface pore sizes. The satisfactory freezing temperature for the collagen-GAG porous particles was thus greater than the −20° C. suggested by Berg, et al. or the −30° C. suggested by Dean, et al. I also discovered the importance of controlling droplet temperature to near 0° C. (not observed by Berg, et al. or Dean, et al.).

EXAMPLE 1

Inoculation of porous microcarriers with CV-1 cells

Five Corning 125 ml (working volume) spinner flasks were used at stirring speeds of 35 and 60 rpm. The flasks were loosely capped during incubation and incubated in a 10% $CO_2$ atmosphere at 37 degrees. The medium was Dulbecco's Modified Eagles Medium (DMEM) (25 mM glucose) with 5% fetal bovine serum (FBS).

Porous collagen-GAG microcarriers were washed once with medium and sedimented at 1500 rpm; 3.75 ml of bed volume were placed in each of two spinner bottles. Medium was delivered to each flask to a total volume of 115 ml. Cytodex 3 was hydrated with PBS, washed once, and autoclaved for 15 min; the microcarriers were transferred to a 50 ml centrifuge tube, washed with complete medium, and sedimented at 1500 rpm. Ten milliliters of Cytodex bed volume was placed in a 125 ml Corning spinner flask. A smaller bed volume of porous microcarriers were used because of the greater capacity of cells which can be grown on a bed of porous microcarriers.

CV-1 were grown to confluence in a 500 cm$^2$ roller bottle, harvested by trypsinization, and diluted to a volume of 50 ml with DMEM, 5% FBS.

Inoculation

Ten ml of inoculum was added to each spinner flask, resulting in a total volume of 125 ml with a final cell concentration of about 8×10$^4$. In addition to the Cytodex and the two porous microcarrier flasks, a control flask contained no microcarriers. During the inoculation period, one porous microcarrier flask was not placed on the stirrer ("Static"), but was stirred at about 30 rpm for about 5 seconds before each sample was taken.

Flasks were removed from the incubators and the microcarriers were allowed to settle for at least 0.5 min. 5 ml samples were taken near the top of the cultures and diluted immediately with 15 ml of Isoton (Coulter). Points were taken at 5, 30, 60, 120, 180, 240 and 570 minutes. Each sample was counted in 0.5 ml aliquots at least twice by Coulter Counter with a 100 µm aperture. Replicate measurements were averaged.

Figure 2:
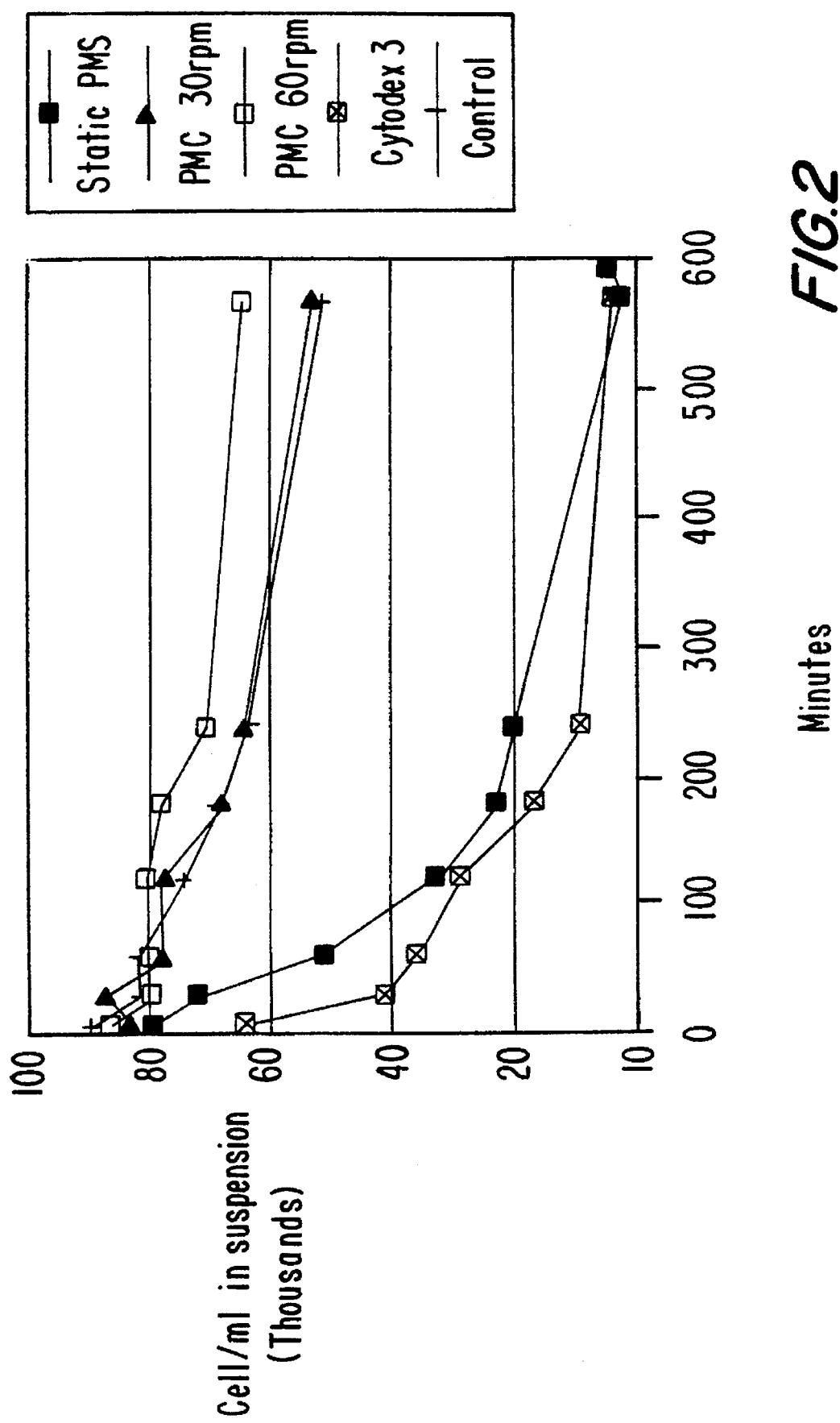
FIG. 2: Kinetics of attachment of CV-1 cells to porous collagen-GAG microcarriers with steady and intermittent agitation. (+) control culture with no microcarriers; (□) Cytodex 3 culture inoculated at 60 rpm; (▶) porous microcarriers inoculated at 30 rpm; (□) porous microcarriers inoculated at 60 rpm; (s) porous microcarriers with "static" inoculation.

Data in FIG. 2 show that the suspended cells in the control culture (no microcarriers) decreased slightly from about 8×10$^4$/ml to about 5×10$^4$/ml over the 570 min incubation period. Suspended cells in the Cytodex culture decreased to about 4×10$^3$/ml over the same time period. The porous microcarrier samples incubated at 30 or 60 rpm show little difference from the control culture, indicating poor cell attachment. The "static" porous microcarrier culture showed a decrease in suspended cells from about 8×10$^4$ to about 2×10$^3$ cells/ml during incubation, indicating that most of the cells attached to the porous microcarriers.

Microscopic examination of the porous microcarriers by crystal violet staining after 9.5 hours of incubation showed that the microcarriers incubated under static conditions were heavily covered with cells too numerous to count (>100 per particle). The porous microcarriers incubated at either 30 or 60 rpm showed very few cells attached (<25).

Figure 3:
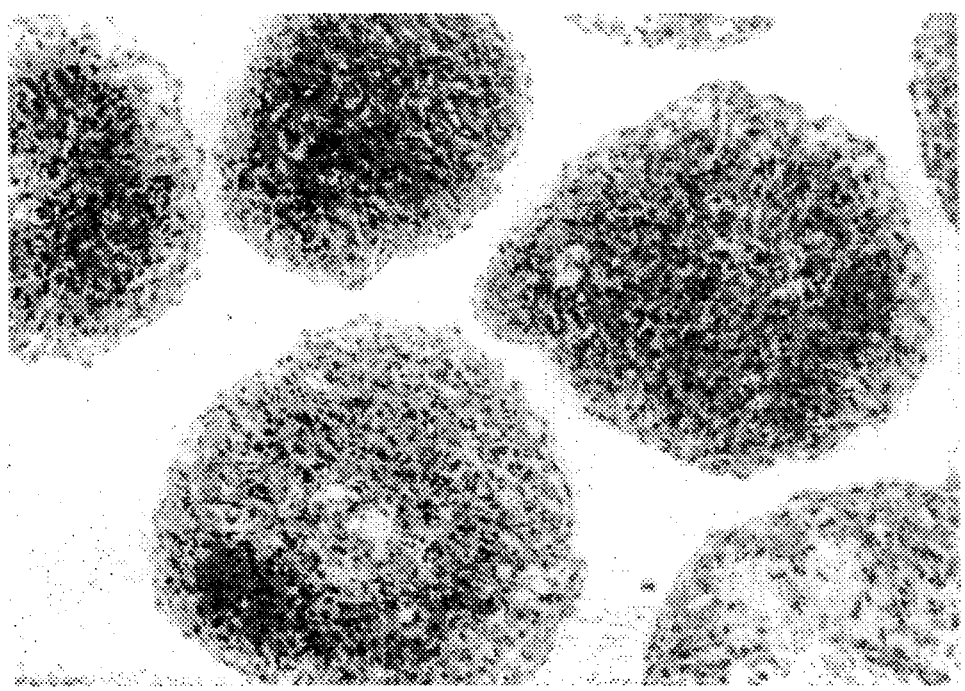
FIG. 3: Micrograph (93× magnification) of a thin section of anchorage-dependent cell line CV-1 after "static" inoculation and 7 days of culture on collagen-glycosaminoglycan porous microcarriers. Beads were fixed in 10% formalin, embedded in glycol methacrylate, cut in 2 µm sections, and stained.
Figure 4:
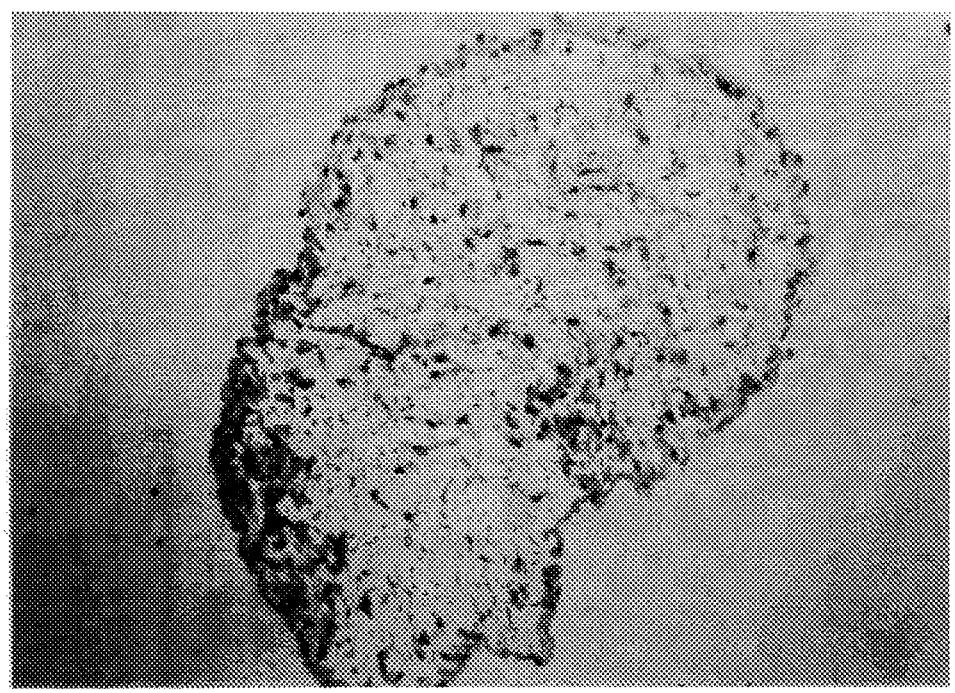
FIG. 4: Micrograph (93× magnification) of a thin section of anchorage-dependent cell line CV-1 after inoculation at 60 rpm and 7 days of culture in on collagen-glycosaminoglycan porous microcarriers. Beads were fixed in 10% formalin, embedded in glycol methacrylate, cut at 2 µm sections, and stained.

Incubation was continued for seven days, after which samples were taken and fixed in 10% formalin and histologically embedded, sectioned, and stained. FIG. 3 shows the high density growth in the "statically" inoculated particles, and FIG. 4 shows much poorer growth in a microcarrier from the culture inoculated and incubated at 60 rpm (the 30 rpm sample was similar).

The sample shown in FIG. 3 indicates that CV-1 cells grow to fill greater than 90% the void volume of the porous particles. If these microcarriers were used in a oxygenated reactor system (such as the one described below) at a bed volume of 40% of the working volume of the reactor, about 240 ml of cells/liter could be supported. For average cell sizes between 12 and 20 µm, this cell concentration would correspond to between 6.4×10$^7$ and 7.5×10$^8$ cells/ml, which is about 16 to 75 times the concentration which can be grown on a suspension of Cytodex microcarriers at 5 g/l (about 4×10$^6$ cells/ml).

This experiment shows that a good inoculation procedure results in dense coverage of the surface of the microcarrier with cells; poor inoculation can be recognized by few attached cells. Good inoculation seems to result in vigorous growth of cells into the particle interior, whereas the fewer cells attaching during a poor inoculation did not result in a well populated interior even after 1 week of incubation.

To limit cell capacity, only about one third of the bed volume of porous microcarriers was used in comparison with Cytodex. Exposed external surface of the Cytodex is about 2000 cm$^2$ per flask for the 10 ml bed volume per flask in this experiment (assuming bead internal volume is about 60% of bed volume). Porous microcarriers will have an exposed external surface (envelope) of about 250 cm$^2$ for the bed volume of 3.5 ml per flask, assuming an average particle diameter of 500 microns and a bead volume of 60% of the bed volume. Thus, if attachment proceeds by initial attachment to the external surface of the microcarriers; attachment rate may be limited because only about 12% as much surface is exposed in the porous microcarrier case.

Hydrodynamic stress on cells attached at the external surface of microcarriers may be estimated by the Kolmogorov radius, which represents the approximate dimensions of the dissipative eddy currents due to turbulence of a stirred system. Because the porous microcarriers are larger than the Cytodex microcarriers (about 180 µm diameter), cells attaching at the porous microcarrier surface may be more sensitive to shear than those on the Cytodex. Only after cells have grown into the interior, are they protected by the porous structure.

The gentle inoculation procedure in Example 1 is not an absolute requirement for a satisfactory culture. My experience has shown that adding cells during steady stirring can be satisfactory, as in Example 2, below.

EXAMPLE 2

Protection of cells in porous microcarriers in vigorous agitation.

The medium used was DMEM (25 mM glucose), supplemented with 5% fetal bovine serum. Solid Cytodex 3 microcarriers (Sigma Cat. C-3275) were hydrated and sterilized according to the instructions from the manufacturer. The bead concentration in the spinner flasks was 4 g/l. The porous microcarriers were hydrated, washed three times with PBS, and left overnight on a tube rocker in serum supplemented medium.

Cell culture.

CV-1 monkey kidney cells were obtained at unknown passage number. Only cells with less than 50 doublings were used in the experiments presented here. The culture flasks were 125 ml Corning spinner flasks which were siliconized using Prosil-28 according to the instructions from the manufacturer (PCR Inc. Gainesville, Fla.). Agitation speeds were calibrated by means of a strobe light. Incubation was at 37° C., in a 10% $CO_2$ atmosphere. CV-1 cells were inoculated on Cytodex at a cell concentration between 5 and 10 cells/bead under continuous agitation at 35 RPM. After attachment and initial growth had occurred, the experiment was started by adjustment of stirring rates. Thereafter, samples were taken daily, the medium was removed the beads were washed once with PBS. Cultures were inoculated on porous microcarriers with 10% (settled volume/total volume) beads at 1×10$^5$ cell/ml total volume. During the period of cell attachment and initial growth, the cultures were agitated at 35 RPM. Cell enumeration was by means of nuclei counting after incubation in 150 mM citric acid, 0.5 g/l crystal violet for at least two days. Because nuclei counting in porous microcarriers is impeded by the three-dimensional cell growth, cell enumeration for the porous microcarriers was by means of a DNA assay.

The DNA assay was performed as follows: 5 ml samples were taken, the medium was removed, the beads were washed once with PBS, and stored frozen at −20° C. The 5 ml sample volume was replaced with fresh medium. At the end of the experiment, the beads were homogenized by sonication using a model W-225/C2 sonicator with 50% duty cycle (Heat systems Ultrasonics Inc. Farmingdale, N.Y.), and the DNA content of the homogenate was determined using a diphenylamine assay (J. L. Johnson, *Manual of Methods for General Bacteriology*, P. Gerhardt, et al., Eds., pp. 456–457, 1981), with calf thymus DNA as a standard. Calf thymus DNA standard was in turn calibrated (7.5×10$^4$ CV-1 cells/µg DNA). Under the conditions of the assay, the collagen matrix usually dissolved. Dissolved collagen did not interfere with the assay.

Figure 5A:
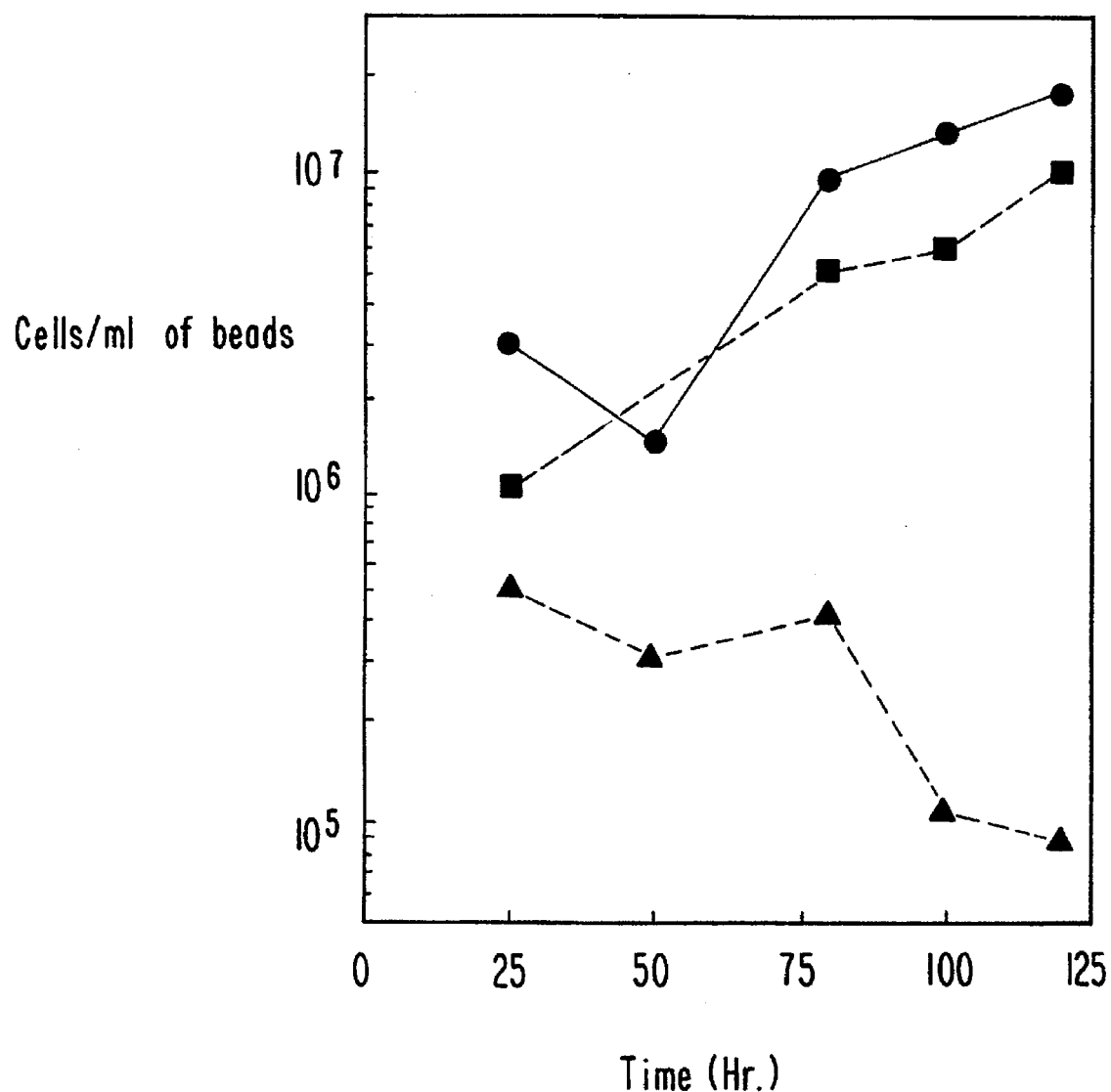
FIG. 5A: Cell growth of CV-1 cells on solid Cytodex 3 microcarriers at different levels of agitation. The microcarrier concentration is 4 g/l, equivalent to about 5.6 ml of settled bed volume per 100 ml. 35 rpm (●); 100 rpm (■); 150 rpm (▲).
Figure 5B:
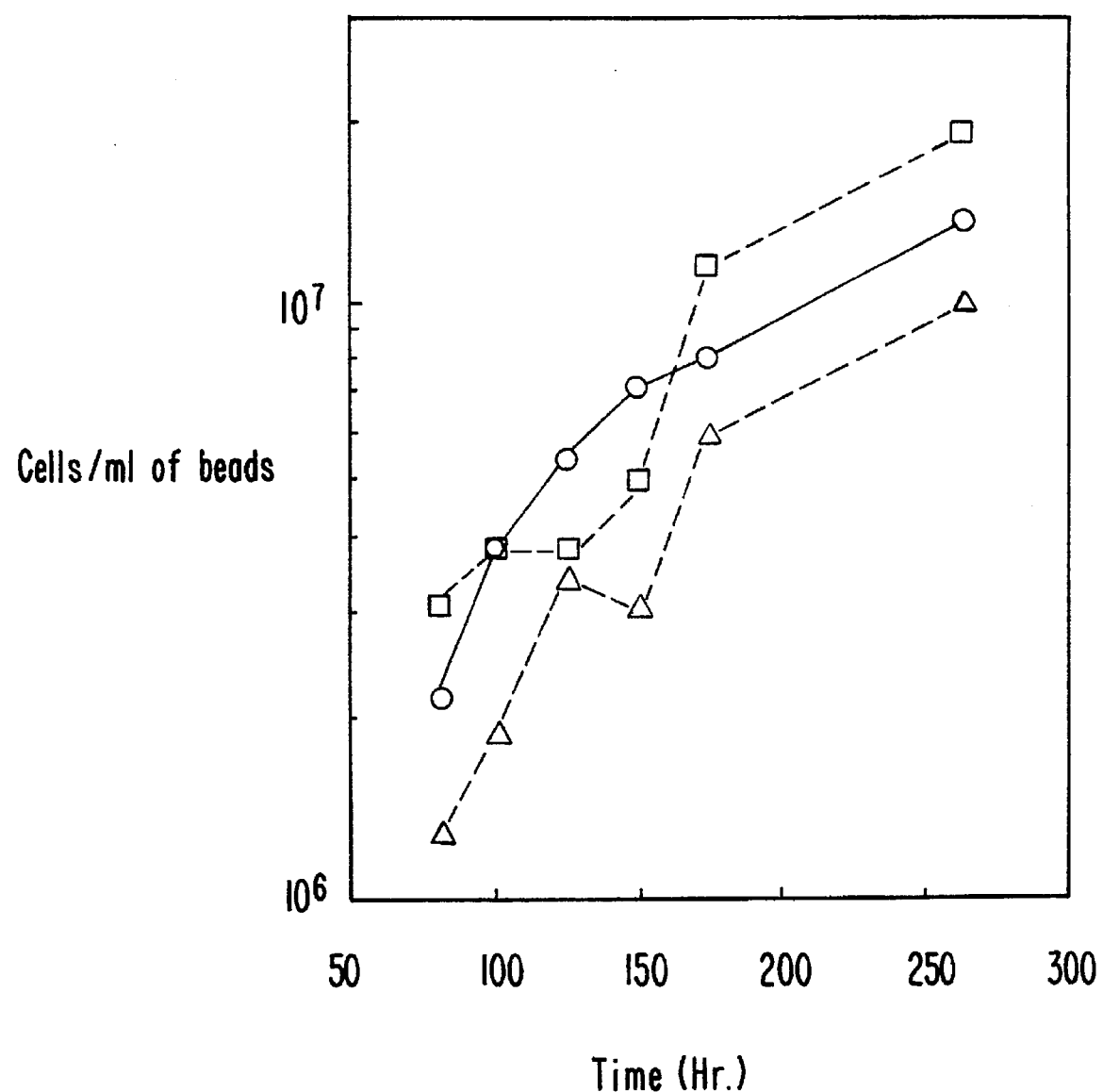
FIG. 5B: Net cell growth of CV-1 cells on porous microcarrier beads at different levels of agitation. The microcarrier concentration is 10 ml of settled bed volume per 100 ml. 35 rpm (o); 101 rpm (□); 158 rpm (△).

In agreement with earlier results (M.S. Croughan, et al., *Biotechnol. Bioeng.*, 29: 130–141 (1987)), cell growth on solid microcarriers is inhibited when the culture is agitated at speeds above 100 RPM (FIG. 5A). However, when CV-1 is cultured on porous microcarriers, at the same levels of power input per unit volume, cell growth appears unaffected by the hydrodynamic stress in the culture (FIG. 5B). This result is significant because the larger beads, if not for their porous nature, should have been more susceptible to shear damage.

Porous beaded microcarriers used in these experiments had diameters of about 400–900 µm and void volume above 99%. This particle size may be near the upper limit of the size which will support oxygen transfer to the cells in the interior, as suggested by experiments on oxygen diffusion in tumor spheroids (R.M. Sutherland, *Science*, 240: 177–184 (1988)). Correspondingly, they should also have a maximum ability to protect cells in the interior based on geometric considerations. In experiments reported here the porous matrix substantially protected the cells from the effects of high agitation rates, allowing cell growth at otherwise prohibitive levels of power input per unit volume.

EXAMPLE 3

Growth of VERO.

Figure 6:
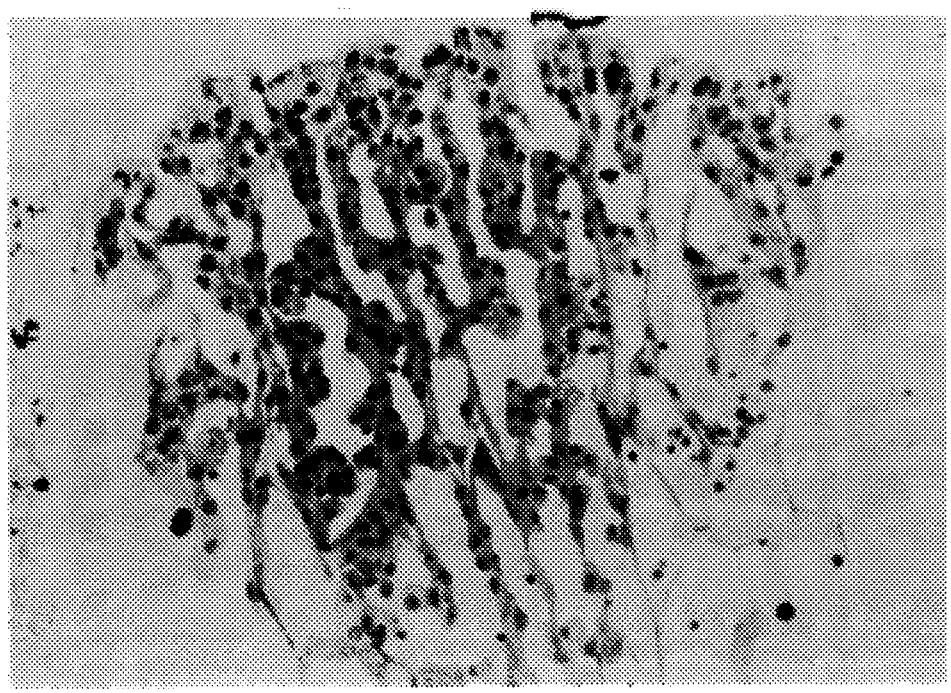
FIG. 6: Micrograph (185× magnification) of a thin section of anchorage-dependent cell line VERO after 31 days of culture in porous collagen-glycosaminoglycan microcarriers.

Not all anchorage-dependent cells will completely fill the void volume of porous microcarriers. FIG. 6 shows a culture of VERO cells cultured in DMEM, 5% FBS after 31 days of culture. Generally, only a single layer of cells grows on the collagen-GAG interior surfaces of the microcarriers. The existence of channels into the interior may permit convective flow of medium into the particle interior in this case. In the same experiment I observed that the growth of VERO into the interior of a large particle (about 1.5 mm) appears to be self limited with the cells concentrated only in the outer half of the radius of the particle, and there was no evidence of necrosis in the most central cells.

EXAMPLE 4

Anchorage-independent cells

Figure 7:
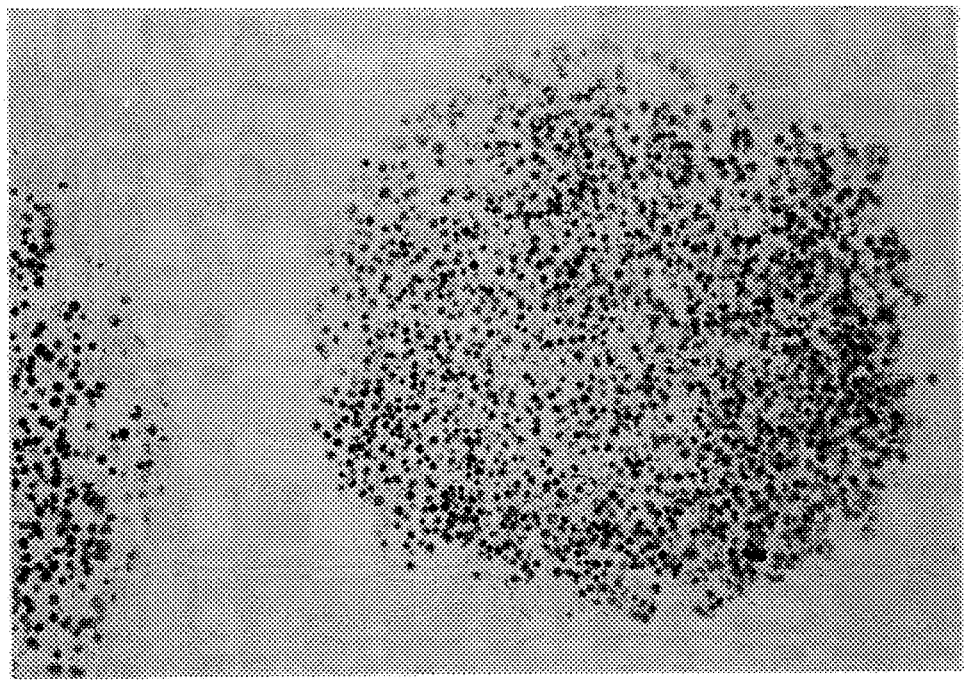
FIG. 7: Micrograph (93× magnification) of a thin section of anchorage-independent cell line H-9 after 21 days of culture in porous collagen-glycosaminoglycan microcarriers.

FIG. 7 shows a section of a porous microcarrier from a culture of lymphoid cell line H-9 after 21 days of spinner flask culture in porous microcarriers. It can be seen that a high density of this anchorage-independent cell is retained in the porous matrix. The porous microcarrier can not only provide mechanical protection to anchorage-independent cells, but can also retain them in a perfused culture system.

In the above examples, low densities of microcarriers were used, and the culture vessels were small spinner flasks. Spinner flasks aerate the culture by diffusion from the head space of the vessel; there is further exchange of oxygen and carbon dioxide between the head space and the controlled atmosphere of the incubator because the vessels were loosely capped. By keeping the concentration of microcarriers low, I avoided exhausting the limited oxygen transfer rate from the head space to the medium by providing for only a limited amount of cell growth. For industrial application, larger culture volumes are needed than can be conveniently aerated from the reactor head space. Also, higher microcarrier concentrations lead to greater economic efficiency. Shear protection of a porous microcarrier permits vigorous stirring and agitation needed to oxygenate a large culture. Additional advantages can be realized at high microcarrier concentrations by replenishing medium through a perfusion culture system to avoid exhausting nutrients. The cell concentrations and shear protection properties observed with porous microcarriers in the above examples can indicate that similar cell biomass concentrations in microcarriers can also be realized in large scale cultures having efficient oxygenation and (optionally) nutrient replenishment. Accordingly, a stirred or air-lift fermenter systems at high microcarrier concentrations, where from about 5 to 50% of the working volume of the reactor consists of microcarrier bed volume, offers an excellent mode of operation. Such a system is described below.

EXAMPLE 5

Figure 8:
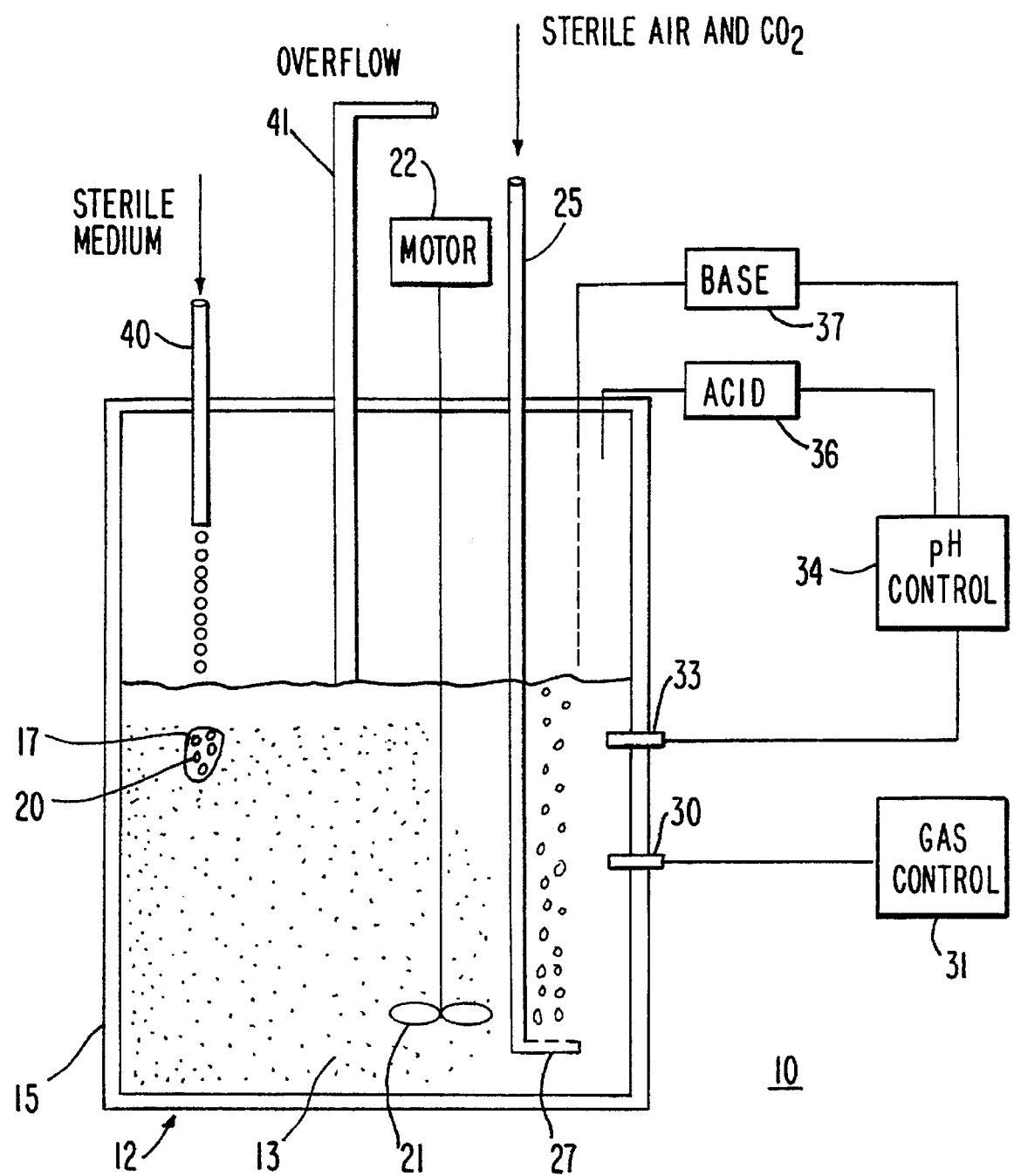
FIG. 8: Schematic representation of a cell culturing system.

FIG. 8 shows a schematic representation of the invention 10 having a reactor 12 in which is contained a quantity of liquid medium 13. Reactor 12 of culture system 10 is provided with a fluid jacket 15 surrounding the reactor through which flows a heated fluid, illustratively water, at a predetermined temperature of between approximately 30° to 40° C. Thus, the temperature of liquid medium 13 is controlled; which control may be achieved by any of several known temperature control systems.

Liquid medium 13 contains suspended therein a multiplicity of matrix particles, such as matrix particle 17 which is shown enlarged and contains thereon a plurality of pores 20. The matrix particles contain voids therewithin (not shown) in which are contained mammalian cells (not shown). In a preferred embodiment of the invention, the matrix particles are maintained in suspension by operating of an impeller 21 which is preferably of the low shear type and is connected to a motor 22 for achieving rotation.

Liquid medium, and the cells contained within the voids of the matrix particles, are oxygenated by a sparging system 25 which contains a sparger 27 which aerates the liquid medium with sterile air and $CO_2$ in this embodiment. The gas contents of the liquid medium are detected by an oxygen probe 30 which senses the quantity of oxygen in the liquid medium and supplies a signal to a gas controller 31.

In addition to monitoring of the oxygen in the liquid medium, pH is detected by a pH probe 33 which is connected to a pH controller 34. pH controller 34 controls the introduction of acidic and basic substances from supplies 36 and 37, respectively. In the drawing, pH controller 34 is increasing the pH level of the liquid medium by adding a basic substance from base supply 37.

New sterilized liquid medium, is added at a controlled rate via a sterile medium input 40. If the level of liquid medium 13 in the culture system exceeds a predetermined level, excess medium is expelled via overflow tube 41. Excess medium expelled via overflow tube 41 may be conducted to a harvest vessel where a desired product may be extracted.

An objective of a practical continuous culture system is to maximize product yield per unit volume of medium. To achieve this, it is oftentimes necessary to minimize the amount of medium maintaining the biomass in the reactor. This may be achieved by controlling the pH and the oxygen by appropriate instrumentation. Additionally, stirring rate must be controlled to achieve desired suspension of the matrix beads, without unduly stressing the cells therein. To optimize oxygen transfer into the matrix, particles must be sufficiently small, (e.g., approximately between 200 to 500 micrometers), and well mixed. Sparging provides the most intimate contact between the matrix and the oxygen introduced via air bubbles.

Although the invention has been described in terms of specific embodiments and applications, persons skilled in the art, in light of this teaching, can generate various embodiments which are to be considered within the scope and spirit of the claimed invention. The invention is only to be limited by the claims which follow and their equivalents.

What is claimed is:

1. A method of making a mass of generally spherical porous matrix particles having a generally isopycnic density with liquid growth medium, a sponge-like character and diameters of less than about 2 millimeters, each particle consisting essentially of a generally homogeneous biologically compatible matrix having a multiplicity of voids therein, the voids representing at least 10 percent of the total volume of the particle, the voids being connected to pores of less than 100 micrometers in diameter which connect the voids to the exterior of the particle, the method comprising the steps of:

(a) dispersing a collagen in an acidic aqueous medium to form an aqueous collagen dispersion;

(b) combining a collagen-precipitating agent with the aqueous collagen dispersion to form an aqueous suspension of a collagenous precipitate;

(c) forming droplets from the aqueous suspension of the collagenous precipitate in a temperature-controlled droplet-formation thermal environment in thermal contact with the aqueous suspension as the droplets are formed, the temperature of the droplet-formation thermal environment being maintained at approximately 0° C.;

(d) immersing the droplets in a temperature-controlled droplet-freezer bath to freeze the droplets, the droplet-freezer bath containing a water-immiscible liquid comprising a mixture of a hydrocarbon and 1,1,2, trichlorotrifluoroethane, the liquid being maintained at a droplet-freezing temperature significantly below 0° C.;

(e) removing the frozen droplets from the droplet-freezer bath;

(f) drying the frozen droplets by sublimation to form porous particles of a collagenous material; and (g) crosslinking the collagenous material in the particles to form porous particles of a biologically compatible crosslinked collagenous material.

2. The method of claim 1 in which the collagen-precipitating agent comprises a glycosaminoglycan.

3. The method of claim 2 in which the glycosaminoglycan contains sulfate groups.

4. The method of claim 3 in which the glycosaminoglycan is chondroitin-6-sulfate.

5. The method of claim 2 in which the collagenous precipitate comprises a coprecipitate of collagen and glycosaminoglycan.

6. The method of claim 1 in which the droplet-freezing temperature of the liquid in the droplet-freezer bath is approximately −9± about 5° C.

7. The method of claim 1 in which the water-immiscible liquid of the droplet-freezer bath consists essentially of a mixture of a hydrocarbon and 1,1,2, trichlorotrifluoroethane.

8. The method of claim 1, wherein porous particles formed have voids representing about 90 percent or more of the total volume of the particle.

9. The method of claim 1, wherein the step of forming droplets comprises forcing the aqueous suspension of the collagenous precipitate through a cannula, the temperature of the cannula being maintained at approximately 0° C. to constitute a temperature-controlled thermal environment.

10. The method of claim 1, wherein the step of crosslinking comprises exposing the collagenous material in the dried particles to aldehyde vapors.

11. The method of claim 1, wherein the hydrocarbon is hexane.

* * * * *